United States Patent [19]

Robillard

[11] Patent Number: 5,436,167
[45] Date of Patent: Jul. 25, 1995

[54] FIBER OPTICS GAS SENSOR

[75] Inventor: Jean J. Robillard, El Paso, Tex.

[73] Assignee: Board of Regents, University of Texas System, Austin, Tex.

[21] Appl. No.: 46,977

[22] Filed: Apr. 13, 1993

[51] Int. Cl.$^6$ ............................................. G01N 21/03
[52] U.S. Cl. ..................................... 436/165; 385/12; 385/128; 422/82.05; 422/82.11; 422/83; 422/88; 422/91; 436/167
[58] Field of Search ............... 422/82.01, 82.05, 82.06, 422/82.08, 82.09, 82.11, 83, 88, 91, 94, 98; 436/165, 172, 167; 385/128, 141, 145, 12

[56] References Cited

U.S. PATENT DOCUMENTS

| | | | |
|---|---|---|---|
| 3,060,307 | 10/1991 | El-Sherif | 385/12 X |
| 4,459,023 | 7/1984 | Reich et al. | 356/237 |
| 4,484,818 | 11/1984 | Houston | 356/432 |
| 4,538,912 | 9/1985 | Shaw, Jr. | 356/366 |
| 4,557,900 | 12/1985 | Heitzmann | 422/55 |
| 4,582,809 | 4/1986 | Block et al. | 422/82.05 |
| 4,661,320 | 4/1987 | Ito et al. | 422/86 |
| 4,689,248 | 8/1987 | Traver et al. | 385/128 |
| 4,718,747 | 1/1988 | Bianchi et al. | 350/96.23 |
| 4,764,343 | 8/1988 | Nyberg | 422/83 |
| 4,815,843 | 3/1989 | Tiefenthaler et al. | 356/128 |
| 4,828,354 | 5/1989 | Yoshiba | 385/128 |
| 4,834,497 | 5/1989 | Angel | 385/128 |
| 4,846,548 | 7/1989 | Klainer | 385/145 |
| 4,849,172 | 7/1989 | Yafuso et al. | 422/55 |
| 4,861,727 | 8/1989 | Hauenstein et al. | 436/136 |
| 4,872,759 | 10/1989 | Stich-Baumeister et al. | 356/432 |
| 4,887,455 | 12/1989 | Payne et al. | 73/27 R |
| 4,931,851 | 6/1990 | Sibbald et al. | 385/12 X |
| 5,028,395 | 7/1991 | Sebille et al. | 422/82.06 |
| 5,093,880 | 3/1992 | Matsuda et al. | 385/128 |
| 5,102,625 | 4/1992 | Milo | 422/82.06 |
| 5,153,931 | 10/1992 | Buchanan et al. | 385/12 |
| 5,201,022 | 4/1993 | Shifflett | 385/128 |
| 5,208,823 | 5/1993 | Patel | 372/50 |
| 5,237,631 | 8/1993 | Gavish et al. | 385/141 |
| 5,251,060 | 10/1993 | Uenishi et al. | 385/145 X |

FOREIGN PATENT DOCUMENTS 8100912  4/1981  European Pat. Off. ......... 422/82.05

OTHER PUBLICATIONS

Robillard, Jean, and Caulfield, H. John., *Industrial Applications of Holography*, Ch. 1, 2, 8 and 11 (1990).

Primary Examiner—Robert J. Warden
Assistant Examiner—Krisanne M. Thornton
Attorney, Agent, or Firm—Arnold, White & Durkee

[57] ABSTRACT

The adsorption of gas on a solid surface can produce considerable variation in the optical properties of the solid surface and eventually lead to the identification of the gas adsorbed. An optical waveguide having at least a portion of its length circumferentially coated with a transparent semiconductor material may function as a gas sensor. The sensor functions by exchanging electrons with a detectable gas brought in proximity with the coating material at reactive sites on the material's surface by the process of adsorption, thereby varying the refractive index of the transparent semiconductor material and altering the ellipticity of a light transmission through the optical waveguide. Substantially monochromatic polarized light is transmitted through the optical waveguide and then quantified by a light detector. A meter or other device connected to the light detector is adjusted to register a variation in the signal received by the light detector, indicating the presence of a detectable gas.

30 Claims, 1 Drawing Sheet

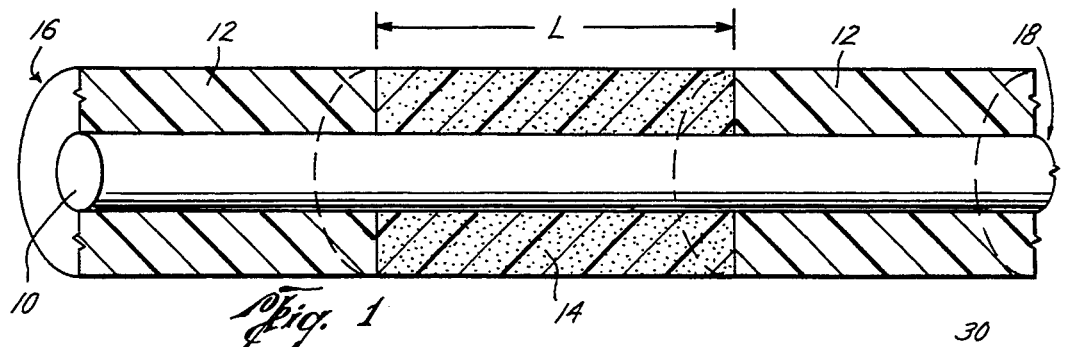
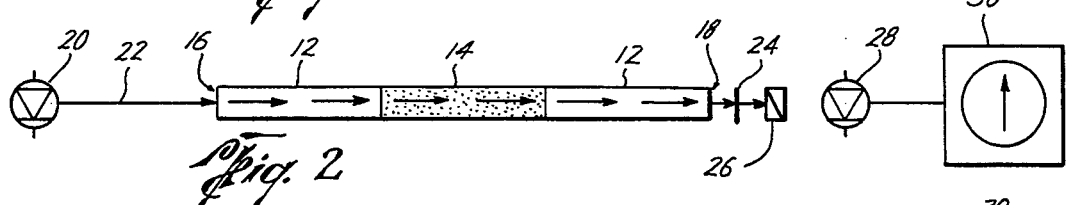
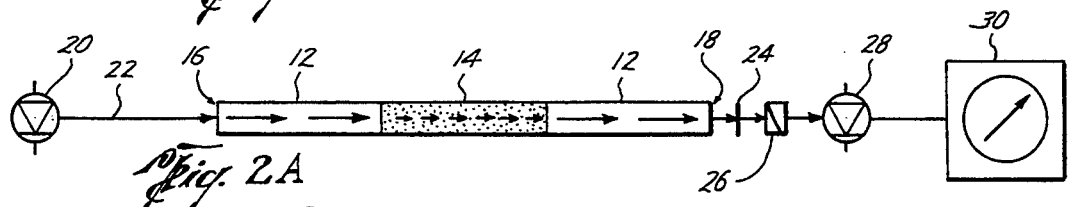
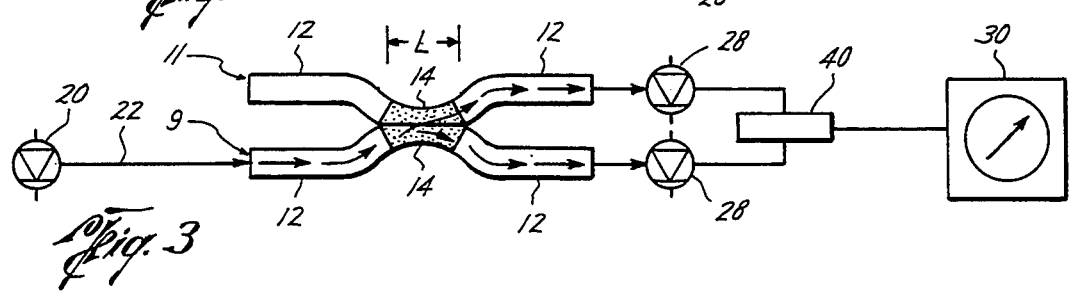
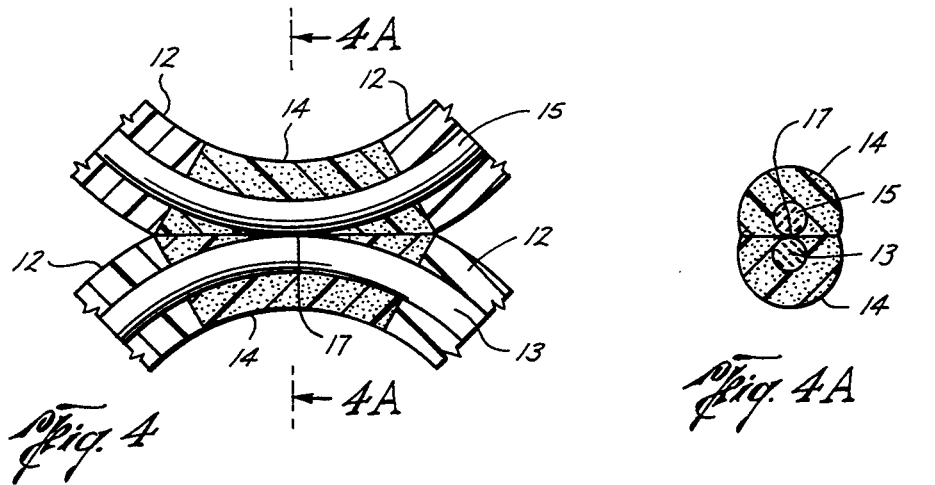

FIBER OPTICS GAS SENSOR

BACKGROUND OF THE INVENTION

This invention relates to a method and apparatus for detecting the presence of a gas, and more particularly to a gas sensor that detects a gas by detecting changes in optical properties of a semiconductor in response to adsorption of the gas on the semiconductor surface.

Many pollutants in the atmosphere are potentially harmful, a number of which have been categorized as most urgent to detect and eliminate. They include particulates ($SiO_2$, asbestos), various oxides such as $NO_x$, $SO_2$, and CO, $CH_4$, Pb, $H_2S$, mercaptans, and organic sulfides, as well as visibility reducing particles such as dust and sand. The levels of various individual pollutants have varied over the past 20 years. For example, carbon monoxide and hydrocarbons have declined, while the nitrogen oxides, which are a major health hazard, are rising sharply. Thus, a need exists for methods and apparatus for accurately measuring and monitoring gases and pollutants in the atmosphere.

Nonheated gas sensors have been devised that avoid some of the dangers associated with heated gas sensors. For example, U.S. Pat. No. 4,661,320 to Ito et al. describes a gas sensor comprising a device by which optical absorption is changed in the presence of hydrogen gas (or a hydrogen-containing compound) and a detecting apparatus is used for detecting the change in optical absorption. The device is made of a laminate of catalytic metal, which causes dissociation of gas molecules when a hydrogen gas is present. As a result, hydrogen protons are injected into a solid compound underlying the metal laminate, causing a corresponding change in the compound's rate of optical absorption. The change in optical absorption is detected by apparatus sensitive to a change in intensity of light transmitted through the device, thereby indicating the presence of a hydrogen gas or hydrogen gas compound.

The injection of hydrogen protons into the solid compound is a chemical reaction, which requires that the protons be energized to diffuse and penetrate and cross the potential barrier to reach a position inside the material. Therefore, a disadvantage of Ito's technique is that energy need be input to sustain the chemical reaction and also to reverse the reaction and restore the transparency of the solid compound.

SUMMARY OF THE INVENTION

Broadly speaking, the present invention contemplates a method and apparatus for detecting the presence of a gas based on the variation of the refractive index of a material as a function of minute quantities of gas adsorbed on its surface. More specifically, the cladding of a fiber optic cable is replaced over a certain length by a variable index material, such as a transparent semiconductor, and exposed to the gas to be detected. On the semiconductor surface, an adsorbed gas is able to play a role comparable to a "dopant" and therefore initiate changes in optical properties of the semiconductor. Certain semiconductor materials are sensitive (in terms of parts per million, or ppm) to the adsorption of specific gases, causing corresponding changes in their physical properties, such as refractive index, polarizability, et cetera. For example, one part of nitrogen dioxide in $10^9$ parts of air can be detected on certain organic semiconductors. This process can be exploited to detect the presence of a gas by monitoring the corresponding changes in the semiconductor material that result from selective gas adsorption, or "chemisorption."

Optical properties are especially suitable for monitoring changes in a semiconductor material in response to an adsorbed gas. The multi-reflection propagation of a light wave along a fiber optic cable is strongly dependent on the index of refraction of the cladding material. To each reflection at the interface between the core and the cladding corresponds an evanescent wave, which penetrates the cladding and contributes to a certain attenuation that depends on the index of refraction of the cladding material. If this index is changed, the intensity of the reflection of the wave will be affected, thereby causing a change in the intensity of the light, its polarization, and the time delay between the central ray and the slowest ray transmitted through the fiber.

With the use of appropriate semiconductor cladding material, certain gases may be selectively detected by quantifying light transmitted through an optical waveguide, such as a fiber optic cable. In a preferred embodiment according to the present invention, a fiber optic cable is partially clad with semiconductor material. An optical-to-electronic detector is coupled to one end of the cable for detecting and quantifying the presence of a gas by detecting the change in a light transmitted through the cable. In this preferred embodiment, the optical-to-electronic detector comprises a quarter-wave plate and an analyzer (for example a Nichol prism) adjacent to the end of the cable. The analyzer receives the polarized light and allows light to pass only when a detectable gas is present. A photodiode located in the optical path of the analyzer can detect the passage of light when a detectable gas is present, and may be electrically connected to a meter and/or alarm to visually and/or audibly indicate the presence of a gas.

In a preferred method according to the present invention, detecting the presence of a gas may be accomplished by transmitting light, preferably from a substantially monochromatic polarized source such as a semiconductor laser diode, through the fiber optic cable, and in turn through a quarter-wave plate and an analyzer, which is positioned to extinguishment of the light transmitted in the absence of a detectable gas. However, when a gas is present and the refractive indices of the semiconductor cladding are correspondingly altered, the ellipticity of the light will also be altered, thus allowing light to pass through the analyzer. This change will be detected by the photodiode and indicated by a device (such as a meter or alarm) electrically connected to the photodiode.

In another preferred embodiment of the present invention, the apparatus comprises a pair of substantially parallel fiber optic cables with the cores coupled at an area between opposing ends of the cables. In this embodiment, the cables are uniformly clad with a semiconductor material over a length proximal to the area of contact between the cores. As in the previously described embodiment, an optical-to-electronic detector is positioned proximal to one end of the cable pair. In this preferred embodiment, the detector comprises a pair of photodiodes, which are in turn connected to a differential amplifier that is electrically connected to a meter and/or alarm.

In a preferred method of gas detection with this apparatus, substantially monochromatic polarized light is transmitted through a first of the cables. The coupling of the cables divides the signal between the first and second fibers, with the total light output of the pair maintained at a constant level. The transmitted light is received by the pair of photodiodes. In the absence of a detectable gas, the differential amplifier will detect a reference difference in the signals received by the photodiode pair, and the meter is adjusted to read "0" or some other reference value. When a gas is adsorbed by the semiconductor cladding, the amount of light transmitted through the coupling region to the second cable will be correspondingly altered. As more gas is adsorbed, more light will enter the second cable through the coupling region. The resulting change in output ratio will be detected by the photodiode pair. The differential amplifier will then detect a signal received by the photodiode pair that will be different from the reference signal, and the meter or alarm will then indicate the presence of a gas.

The present invention therefore comprises an improved method and apparatus for detecting the presence of a variety of gases. Unlike previously known gas sensor devices, the apparatus contemplated by the present invention does not involve a chemical ion interaction, but rather a straight electron interaction, which is faster and leads to quicker detection of gases. Additionally, no input energy is required to initiate the adsorption process; the gas molecules have enough free energy to place themselves in a favorable position in the semiconductor material. A further advantage is that the process of the present invention is reversible by photodesorption.

Further objects, features, and advantages of the present invention will be apparent from the following detailed description when taken in conjunction with the accompanying drawings.

BRIEF DESCRIPTION OF THE DRAWINGS

So that the manner in which the herein described advantages and features of the present invention, as well as others which will become apparent, are attained and can be understood in detail, more particular description of the invention summarized above may be had by reference to the embodiments thereof that are illustrated in the appended drawings, which form a part of this specification.

It is to be noted, however, that the appended drawings illustrate only exemplary embodiments of the invention and are therefore not to be considered limiting of its scope, for the invention may admit to other equally effective embodiments.

FIG. 1 is a partial cross-sectional view of an optical waveguide, illustrating a fiber optic cable having a core circumferentially coated with cladding material except over an exposed length, which is coated with a suitable semiconductor material.

FIG. 2 is a diagrammatic view of a gas sensor in accordance with one embodiment of the present invention in the absence of a gas to be detected.

FIG. 2A is a diagrammatic view of a gas sensor in accordance with one embodiment of the present invention in the presence of a gas to be detected.

FIG. 3 is a diagrammatic view of a gas sensor in accordance with another embodiment of the present invention in the presence of a gas to be detected.

FIG. 4 is a cross-sectional view of the fiber optic cables of the embodiment depicted in FIG. 3.

FIG. 4A is a cross-sectional view along plane 4A—4A of FIG. 4.

DETAILED DESCRIPTION OF THE PREFERRED EMBODIMENTS

Turning now to the drawings, FIG. 1 is a partial cross-sectional view of an optical waveguide in accordance with the present invention, illustrating fiber optic cable 8 having core 10 circumferentially coated with cladding material 12 except over an exposed length L, which is coated with suitable semiconductor material 14. A preferred thickness of the semiconductor coating is approximately 0.5 microns. A preferred length of fiber optic cable 8 is between 2 and 3 centimeters, with the preferred magnitude of exposed length L less than 1 cm, and more preferably about 0.5 centimeters. Cladding material 12 is of common design, preferably comprised of Ge doped quartz.

The choice of semiconductor material 14 will depend on the gas desired to be detected. Due to their optical transparency, organic semiconductors are preferred. A table of exemplary corresponding gas/semiconductor pairs is shown below. It is to be understood, however, that the pairs listed in the Table are provided by way of example only.

TABLE

| EXEMPLARY GAS/SEMICONDUCTOR PAIRS | |
|---|---|
| GAS | SEMICONDUCTOR |
| $H_2S$ | Cu (II) Phtalocyanine |
| $O_3$ | Cu (II) Phtalocyanine |
| $CH_2{=}CH_2$ | Polypyrrole |
| $NO_2$ | Polyaminoquinone |
| Hydrazine | Co (III) dithiooxamide |

FIG. 2 is a diagrammatic view of an embodiment of a gas sensor of the present invention illustrating an absence of a gas to be detected. In a preferred method of use, light emitting diode 20 emits light beam 22, which is preferably monochromatic and polarized, into the light reception end 16 of fiber optic cable 8. Suitable devices for emitting substantially monochromatic-polarized light include a laser diode, model number 780, manufactured by Sharp Electronics Corp., Sharp Plaza, Mahwah, NJ 07340. As in FIG. 1, fiber optic cable core 10 is circumferentially coated with cladding material 12 except over exposed length L, where it uniformly is clad with semiconductor material 14. Light beam 22 traverses fiber optic core 10 until it reaches light exit end 18. Light beam 22 then passes through quarter-wave plate 24 and is received by analyzer 26, which may be, for example, a Nichol prism. In the absence of a detectable gas, analyzer 26 is preferably positioned so as to extinguish light beam 22. With analyzer 26 so positioned, photodiode 28, which may be a silicon photodiode, for example model number EGG:HUV 100, will thus not receive a light signal. In turn, meter 30, which is electrically connected to photodiode 28, will receive no electrical signal from photodiode 28, and its reading will thus indicate the absence of a detectable gas. Meter 30 may be any type of meter capable of measuring current in the mA range. Alternatively, an alarm or other type of indicating device may be substituted for, or connected in parallel with, meter 30.

In the presence of a gas to be detected, as illustrated in FIG. 2A, the ellipticity of light beam 22 will be affected by the change in the index of refraction of semiconductor cladding 14 as a result of the adsorption of the gas. Thus, after passing through quarter-wave plate 24, the altered light beam will now be permitted to pass through analyzer 26 and will then be detected by photodiode 28. Meter 30 will visually indicate the reception of light by photodiode 28, and thus the presence of a detectable gas.

The adsorption process monitored in the claimed invention involves an adsorption interaction, or the building of a chemical bond between reactive sites on the surface of the adsorbing molecule, also known as "chemisorption." In this process, electrons are transferred between the adsorbed species (the gas) and the adsorbant (the semiconductor material), with a binding energy corresponding to the adsorption bonds. Reversibility (desorption) requires an input of energy sufficient to break the adsorption bond (bond energy). This energy can be provided by heat (thermodesorption) or by light (photodesorption). An increase in temperature will increase the adsorption process (and thus the rate of electron exchange) to a maximum; as the temperature increases beyond that point, the adsorbates desorb thermally at rates determined by the binding energies of the adsorbates.

The present invention contemplates the use of disposable sensor fibers; however, if continuous use of the sensor fibers is desired, photodesorption is generally a preferred method of reversing the adsorption process. Photodesorption will take place by illuminating the semiconductor area with UV light from a lateral source.

Because of its electronic structure, a semiconductor is very susceptible to change properties as a result of the electron transfer that occurs when a gas is adsorbed on its surface. Electrons in the gas are attracted to reactive sites on the surface of the semiconductor, which correspond to structural defects near the surface, "dangling bonds," or unsaturated bonds. When a gas is adsorbed to the semiconductor, the chemisorbed atoms or molecules produce a space charge at the surface of the adsorbant. To neutralize this charge, electrons are exchanged with the solid at levels varying with the density of free carriers in the solid. If this density is low, the exchange takes place at greater depth. For example, with a semiconductor having a free carrier density of $10^{15}$ cm$^{-3}$, the neutralization of a surface charge of $10^{11}$ cm$^{-2}$ will involve a $10^{-4}$ cm zone in the solid. As a result, a potential barrier is formed near the surface of the semiconductor. The position of the Fermi level in the energy diagram for the semiconductor is affected by these surface changes.

The change in index of refraction of a semiconductor material in response to an adsorbed gas can be detected optically, based on the following principles. The reflection of a monochromatic light beam (e.g., $\lambda=5461$ Å) of known ellipticity against a surface with or without an adsorbed layer leads to a change in ellipticity. If the light waves are decomposed into two components, both normal to the plane of propagation, one component (p) is in the plane of incidence, the other (s) is normal to the plane of incidence. The waves are characterized by an amplitude ($A_{ip}$ and $A_{is}$ for incident light, and $A_{rp}$ and $A_{rs}$ for reflected light) and by a phase ($\delta_{ip}$ and $\delta_{is}$ for incident light, and $\delta_{rp}$ and $\delta_{rs}$ for reflected light).

The reflection causes both the amplitudes (and therefore the amplitude ratio $A_p/A_s$), and the phases (and therefore the phase difference $\delta_p - \delta_s$) to change. However, the presence of an adsorbed layer as a result of the chemisorption process described above leads to an additional phase change, dependent on the thickness and the optical constants of the adsorbed layer. It also leads to an additional amplitude change, which depends on the layer thickness and furthermore on the light absorption of the substrate. Usually the shift of the phase difference is more important than the shift of the amplitude ratio.

The measurement of the ellipticity results from the measurement of two angles:

$$\Delta = (\delta_{rp} - \delta_{rs}) - (\delta_{ip} - \delta_{is}) \quad (1)$$

and $$\Psi = \tan^{-1}\left[\frac{A_{rp}}{A_{rs}} - \frac{A_{ip}}{A_{is}}\right] \quad (2)$$

The claimed invention focuses on detection of the change in ellipticity of the reflected light to detect the corresponding presence of an adsorbed gas. The variation of ellipticity is due to the multi-reflections of the light at the core-semiconductor interface. The variation of intensity measured at the output of the fiber is a result of the analysis of the ellipticity by the system's quarter-wave plate polarizer and analyzer at the end of the fiber (i.e., the analyzer is oriented to extinguish the light transmitted in the absence of a detectable gas).

The apparatus illustrated in FIGS. 1 and 2 represents only one possible embodiment of the present invention. The change in refractive index of a semiconductor material as a result of the aforementioned chemisorption process may be exploited in other ways to detect the presence of a gas. FIG. 3 is a diagrammatic view of another embodiment of the present invention in the presence of a gas to be detected. In a preferred method of use, as in the previously described embodiment, light emitting diode 20 emits light beam 22, which is preferably monochromatic and polarized. Light beam 22 enters a first fiber optic cable 9. Both cables 9 and 11 are circumferentially coated with cladding material 12 except over exposed length L, where they are uniformly clad with semiconductor material 14. Cables 9 and 11 are coupled such that cores 13 and 15 are exposed to each other, as illustrated in FIG. 4A, which is a cross-sectional view along plane 4A—4A of FIG. 4. Exposed length L extends along the length of the coupling between the cores 13 and 15, as illustrated in FIG. 4.

In the absence of a detectable gas, the beam will traverse through cable 9, and a portion of the beam will enter cable 11 through the point of coupling of fiber cores 13 and 15. Light will then be transmitted from both cables 9 and 11, and be received by photodiode pair 28. Differential amplifier 40 (which may be, for example, an Analog Device model 741, manufactured by One Technology Way, Northwood, MA 02062-9106) is electrically connected to photodiode pair 28. A reference signal from the differential amplifier 40 is established, and meter 30, which is electrically connected to differential amplifier 40, is adjusted to register the absence of a detectable gas. When a detectable gas is present, however, the chemisorption process will alter the refractive index of the semiconductor cladding, resulting in a greater transfer of light to cable 11 through coupling interface 17. Differential amplifier 40 will thus receive a signal from photodiode pair 28 that differs from the reference signal, and meter 30 will visually indicate this difference and thus the presence of a detectable gas.

Because the embodiment depicted in FIG. 3 measures the differential signal received from the fiber optic pair, changes in the rate or amount of adsorption caused by fluctuating environmental temperatures will not affect the readings (assuming the temperature does not rise to a level sufficient to cause complete thermodesorption). Accordingly, for applications where temperatures may be expected to fluctuate, this embodiment would be preferred over the first described single-cable embodiment.

The present invention has been disclosed in connection with specific embodiments. However, it will be apparent to those skilled in the art that variations from the illustrated embodiments may be undertaken without departing from the spirit and scope of the invention. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of parts. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. An apparatus for detecting the presence of a gas for use with a source of elliptically polarized light, comprising:
   an optical waveguide having a circumference; and
   a transparent variable index means deposited in a layer over at least a portion of the circumference of said optical waveguide for exchanging electrons with a gas to be detected at reactive sites on the surface of said variable index means by the process of adsorption, thereby varying the refractive index of said variable index means and altering the ellipticity of a light transmitted through the optical waveguide as a function of the presence of said gas.

2. The apparatus of claim 1, wherein said optical waveguide comprises a fiber optic cable with an optical core coated circumferentially with cladding material over a portion of the length of said cable, and coated with said variable index means in a layer over another portion of the length of said cable.

3. The apparatus of claim 1, wherein said variable index means comprises an organic semiconductor.

4. The apparatus of claim 1, further comprising a light emitting means for emitting substantially monochromatic polarized light through a first end of said optical waveguide, said polarized light being elliptically polarized.

5. The apparatus of claim 4, further comprising an optical-to-electronic detector, which comprises:
   polarizing means optically coupled to a second end of said optical waveguide for converting the components of light transmitted through said optical waveguide into plane polarized light;
   analyzing means for receiving plane polarized light from said polarizing means and selectively allowing the passage of said light according to the ellipticity of said received light;
   light detecting means for detecting light selectively passed through said analyzing means; and
   a meter electrically connected to said light detecting means.

6. A system for detecting the presence of a gas, comprising:
   an optical light source;
   an optical waveguide having an input end and an output end, said input end elliptically coupled to said light source, said optical waveguide having a circumference;
   transparent variable index means deposited along at least a portion of the circumference of said waveguide for exchanging electrons with a gas to be detected at reactive sites on the surface of said variable index means by the process of adsorption, thereby varying the refractive index of said variable index means and altering the ellipticity of a light transmitted through the optical waveguide; and
   optical-to-electronic detector means optically coupled to the output end of the waveguide for detecting and quantifying the presence of a gas to be detected by detecting a change in the ellipticity of a light transmitted through said optical waveguide.

7. The system of claim 6, wherein said variable index means comprises an organic semiconductor material.

8. An apparatus for detecting the presence of a gas, comprising:
   a pair of optical waveguides comprising a first optical waveguide optically coupled to a second optical waveguide at a contact area, each said optical waveguide having a circumference;
   transparent variable index means deposited in a layer over at least a portion of the circumference of each of said optical waveguides proximal said contact area for exchanging electrons with a gas to be detected at reactive sites on the surface of said variable index means by the process of adsorption, thereby varying the refractive index of said semiconductor material and altering the ratio of a light transmission through said optical waveguides; and
   optical-to-electronic detector means located at a first end of said pair of optical waveguides for detecting and quantifying the presence of a gas to be detected by detecting a change in said ratio of light transmitted through said optical waveguides.

9. The apparatus of claim 8, wherein said variable index means comprises an organic semiconductor.

10. The apparatus of claim 8, further comprising a light emitting means for emitting substantially monochromatic, polarized light through a second end of said first optical waveguide.

11. The apparatus of claim 8, wherein said first and second optical waveguides are fiber optic cables, each further comprising a fiber optic core circumferentially surrounded by cladding material over a portion of the length of each of said cables and coated with said variable index means in a layer over another portion of the length of each of said cables proximal said contact area.

12. The apparatus of claim 11, said optical-to-electronic light detector means further comprising:
   light detector means optically coupled to an output end of each of said pair of optical waveguides for measuring an intensity of light transmitted through each of said first and second optical waveguides, respectively;
   differential amplifier means electronically coupled to each of said light detector means for measuring a difference in the ratio of light intensity received by said light detector means; and
   a meter electronically coupled to said differential amplifier means.

13. A method of detecting gas, comprising the steps of:
   providing an optical waveguide upon which transparent semiconductor material has been deposited in a sensor layer over at least a portion of a circumference of said optical waveguide;
   placing said semiconductor-coated optical waveguide in a chamber;
   propagating polarized light through said optical waveguide;
   detecting and quantifying light transmitted from said optical waveguide;
   allowing a gas to be detected to enter said chamber;
   reacting said gas with said semiconductor sensor layer whereby said semiconductor material exchanges electrons in said gas at reactive sites on the surface of said semiconductor material by the process of adsorption, thereby varying the refractive index of said semiconductor material and alters the ellipticity of said light propagated through the optical waveguide; and
   detecting a change in said ellipticity of said light transmitted from said optical waveguide in the presence of said gas.

14. The method of claim 13, wherein said transparent semiconductor material is organic.

15. The method of claim 13, said propagating step further comprising:
   providing a light emitter means for emitting substantially monochromatic polarized light.

16. The method of claim 13, said detecting and quantifying step further comprising the steps of:
   converting the components of light transmitted from said optical waveguide into plane polarized light;
   modulating the transmission of said light transmitted from said optical waveguide; and
   selectively detecting the presence of said light according to the ellipticity of said light.

17. The method of claim 16, wherein said change-detecting step further comprises positioning an analyzer means optically coupled to an output end of said optical waveguide to allow light to be detected only when a gas to be detected has become adsorbed on the surface of said semiconductor sensor layer.

18. A method of detecting gas, comprising the steps of:
   providing a pair of optical waveguides comprising a first optical waveguide optically coupled to a second optical waveguide at a contact area, said first and second optical waveguides each having a transparent semiconductor material deposited in a layer over at least a portion of its circumference proximal said contact area;
   placing said optical waveguide pair in a chamber;
   transmitting polarized light through said first optical waveguide;
   detecting and quantifying light transmitted through said optical waveguide pair;
   allowing a gas to be detected to enter said chamber;
   reacting said gas with said transparent semiconductor layer whereby said semiconductor material exchanges electrons with said gas at reactive sites on the surface of said semiconductor material by the process of adsorption, thereby varying the refractive index of said semiconductor material and altering the ratio of said light transmission through said optical waveguides; and
   detecting a change in said ratio of said light transmitted from said optical waveguides in the presence of said gas.

19. The method of claim 18, said transmitting step further comprising:
   providing a light emitting means for emitting substantially monochromatic polarized light.

20. The method of claim 18, wherein said transparent semiconductor material is organic.

21. The method of claim 18, said detecting and quantifying step further comprising the steps of:
   providing a pair of photodiodes comprising a first photodiode optically coupled to said first optical waveguide and a second photodiode optically coupled to said second optical waveguide;
   quantifying a ratio of light intensity received by said photodiode pair; and
   receiving a reference ratio value in the absence of a detectable gas; and
   indicating when said ratio of light intensity received by said photodiode pair differs from said reference ratio value.

22. An apparatus for detecting the presence of a gas for use with a source of light, comprising:
   an optical waveguide having a circumference, a light-input end and a light-emitting end; and
   a variable index means deposited in a layer over at least a portion of the circumference of said optical waveguide for altering the ellipticity of a light transmission through the optical waveguide as a function of the presence of said gas.

23. The apparatus of claim 22, wherein said variable index means comprises an organic, transparent semiconductor material.

24. The apparatus of claim 23, wherein said semiconductor material is selected from the group consisting of Cu (II) Phtalocyanine, Polypyrrole, Polyaminoquinone, and Co (III) dithiooxamide.

25. The apparatus of claim 22, further comprising an optical-to-electronic detector, which comprises:
   polarizing means optically coupled to said light-emitting end of said optical waveguide for converting the components of light transmitted into said light-input end and through said optical waveguide into plane polarized light;
   analyzing means for receiving plane polarized light from said polarizing means and selectively allowing the passage of said light according to the ellipticity of said received light;
   light detecting means for detecting light selectively passed through said analyzing means; and
   a meter electrically connected to said light detecting means.

26. An apparatus for detecting the presence of a gas for use with a source of light, comprising:
   an optical waveguide having a circumference; and
   a transparent, organic semiconductor material deposited in a layer over at least a portion of the circumference of said optical waveguide.

27. The apparatus of claim 26, wherein said semiconductor material is selected from the group consisting of Cu (II) Phtalocyanine, Polypyrrole, Polyaminoquinone, and Co (III) dithiooxamide.

28. An apparatus for detecting the presence of a gas, comprising:
   a pair of optical waveguides comprising a first optical waveguide optically coupled to a second optical waveguide at a contact area, each said optical waveguide having a circumference;

variable index means deposited in a layer over at least a portion of the circumference of each of said optical waveguides proximal said contact area for altering the relative proportion of a light transmission through each of said optical waveguides in response to adsorption of a gas by said variable index means; and optical-to-electronic detector means located at a first end of each of said pair of optical waveguides for detecting and quantifying the presence of a gas to be detected by detecting a change in a ratio of light transmitted through each of said optical waveguides, respectively.

29. The apparatus of claim 28, wherein said variable index means comprises a transparent, organic semiconductor.

30. The apparatus of claim 28, said optical-to-electronic light detector means further comprising:

light detector means optically coupled to an output end of each of said pair of optical waveguides for measuring an intensity of light transmitted through each of said first and second optical waveguides, respectively;

differential amplifier means electronically coupled to each of said light detector means for measuring a difference in a ratio of light intensity received by said light detector means; and a meter electronically coupled to said differential amplifier means.

* * * * *

UNITED STATES PATENT AND TRADEMARK OFFICE
CERTIFICATE OF CORRECTION

PATENT NO.   :   5,436,167
DATED        :   July 25, 1995
INVENTOR(S)  :   JEAN J. ROBILLARD It is certified that error appears in the above-identified patent and that said Letters Patent is hereby corrected as shown below:

At column 8, line 3, delete "elliptically" and insert --optically-- therefor.

Signed and Sealed this

Tenth Day of October, 1995

BRUCE LEHMAN

Attest:

Attesting Officer     Commissioner of Patents and Trademarks